United States Patent
Endara et al.

(12) 
(10) Patent No.: US 7,534,253 B2
(45) Date of Patent: May 19, 2009

(54) CLEVIS ASSEMBLIES FOR MEDICAL INSTRUMENTS AND METHODS OF MANUFACTURE OF SAME

(75) Inventors: Christopher D. Endara, Miami, FL (US); Otto E. Anderhub, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 758 days.

(21) Appl. No.: 10/731,153

(22) Filed: Dec. 10, 2003

(65) Prior Publication Data

US 2005/0131312 A1 Jun. 16, 2005

(51) Int. Cl.
*A61B 17/28* (2006.01)
(52) U.S. Cl. .................................... 606/208
(58) Field of Classification Search ............... 128/751, 128/752, 749; 606/205–210, 211, 170, 174
See application file for complete search history.

(56) References Cited

U.S. PATENT DOCUMENTS 5,482,054 A * 1/1996 Slater et al. ............... 600/564
5,707,392 A 1/1998 Kortenbach
5,716,374 A 2/1998 Francese et al.
5,722,421 A 3/1998 Francese et al.
6,206,903 B1 3/2001 Ramans
6,964,662 B2 * 11/2005 Kidooka ...................... 606/52
2002/0013595 A1 1/2002 Yamamoto
2005/0054946 A1 * 3/2005 Krzyzanowski ............. 600/564

FOREIGN PATENT DOCUMENTS

DE 100 51 652 A1 10/2000
DE 100 56 946 A1 11/2000

OTHER PUBLICATIONS

PCT International Search Report and Written Opinion in PCT/US2004/038237, dated Apr. 22, 2005.

* cited by examiner

*Primary Examiner*—Kevin T Truong
(74) *Attorney, Agent, or Firm*—Finnegan, Henderson, Farabow, Garrett and Dunner LLP

(57) ABSTRACT

Embodiments of the invention relate to endoscopic instruments. More particularly, embodiments of the invention relate to features on the clevis portion of endoscopic instruments. The clevises may be formed from a sheet material to obtain a substantially cylindrical end and at least one clevis arm. The clevis features may include an axle having at least one flared end to engage a clevis arm, one or more U-shaped grooves on the clevis arms to receive an axle, and stiffening ribs to strengthen the clevis arms.

29 Claims, 8 Drawing Sheets

CLEVIS ASSEMBLIES FOR MEDICAL INSTRUMENTS AND METHODS OF MANUFACTURE OF SAME

DESCRIPTION OF THE INVENTION

1. Field of the Invention

Embodiments of the invention relate to medical devices, for example endoscopic instruments. More particularly, embodiments of the invention relate to features on the distal clevis portion of such devices and instruments. The clevises may be stamped from a sheet material and formed to obtain a substantially cylindrical end and at least one clevis arm.

2. Background of the Invention

Endoscopic medical devices may be used in cooperation with an endoscope to perform a medical procedure on a patent. For example, an endoscopic biopsy forceps may be used for taking tissue samples from the human body for analysis. Endoscopic instruments typically include a proximal handle, a distal end effector assembly, and a long, slender, flexible member connecting the handle to the distal assembly. The elongate member is covered with a PTFE, FEP or polyolefin sheath along substantially its entire length. The member may include a pair of axially displaceable control wires extending therethrough. The control wires may be flexible and longitudinally inelastic, and may be formed from metal such as steel. The control wires are coupled to on their proximal ends to a portion of the handle and on their distal ends to a portion of the end effector assembly.

An endoscopic medical procedure is typically accomplished in connection with an endoscope which is inserted into a body and guided by manipulation to the procedure site. The endoscope typically includes a long narrow flexible tube with an optical lens and a narrow lumen for receiving the endoscopic medical device, for example a biopsy forceps. The practitioner guides the endoscope to the procedure site, with appropriate imaging through use of the optical lens, and inserts the endoscopic medical device through the lumen of the endoscope to the procedure site. While viewing the procedure site through use of the optical lens of the endoscope, the practitioner manipulates the actuating handle cause the end effector, for example, biopsy forceps jaws, to perform the medical procedure. After the procedure, the practitioner and/or an assistant carefully withdraws the medical instrument from the endoscope.

The distal assembly of many endoscopic instruments include a clevis that connects the distal assembly to the elongate member and also holds the distal end effectors, such as biopsy forceps jaws. One current cast clevis design has two opposing distal arms. An axle protrudes from one of the distal arms, while the opposing distal arm has a through hole. When the jaws are placed onto the axle, the opposing distal arm is folded over to place the axle in the through hole, and then the end of the axle protruding past the through hole is riveted so as to prevent the distal arms from spreading. Other clevis arrangements are shown and described in U.S. Pat. No. 5,716,374, the complete disclosure of which is incorporated by reference herein.

SUMMARY OF THE INVENTION

An embodiment of the invention includes a clevis assembly for a medical instrument. The medical instrument includes a clevis having a base and a plurality of arms extending from the base and an axle to extend between the plurality of arms. Each of the plurality of arms is configured to accommodate a portion of the axle and an end of the axle includes a flared portion to engage an outer surface of one of the plurality of arms.

In another embodiment, the invention includes a medical instrument including a handle portion, an end effector assembly, and an elongate member connecting the handle portion to the end effector assembly. The end effector assembly includes a clevis having a base and a plurality of arms extending from the base and an axle to extend between the plurality of arms. Each of the plurality of arms is configured to accommodate a portion of the axle and an end of the axle includes a flared portion to engage an outer surface of one of the plurality of arms.

In a further embodiment, the invention includes a method of manufacturing an end effector assembly of a medical instrument. The method includes manipulating a sheet of material to form a clevis, the clevis including a base and a plurality of arms extending from the base and mounting an axle to the plurality of arms, the axle holding an end effector and including a first flared portion at a first end of the axle. Mounting the axle includes engaging the first flared portion with an outer surface of one of the plurality of arms.

In yet another embodiment, the invention includes a clevis for a medical instrument including a base and a plurality of arms extending from the base, at least one of the plurality of arms defining a groove configured to receive an axle.

In still another embodiment, the invention includes a medical instrument including a handle portion, an end effector assembly, and an elongate member connecting the handle portion to the end effector assembly. The end effector assembly includes a base and a plurality of arms extending from the base, at least one of the plurality of arms defining a groove configured to receive an axle.

In a still further embodiment, the invention includes a method of manufacturing a clevis of a medical instrument, the method including manipulating a sheet of material to form a clevis, the clevis including a base and a plurality of arms extending from the base, at least one of the plurality of arms defining a groove configured to receive an axle.

In another embodiment, the invention includes a clevis for a medical instrument including a base and a plurality of arms extending from the base. At least one of the plurality of arms includes a reinforcing portion.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to embodiments of the invention, examples of which are illustrated in the accompanying drawings. Wherever possible, the same reference numbers will be used throughout the drawings to refer to the same or like parts.

Figure 1:
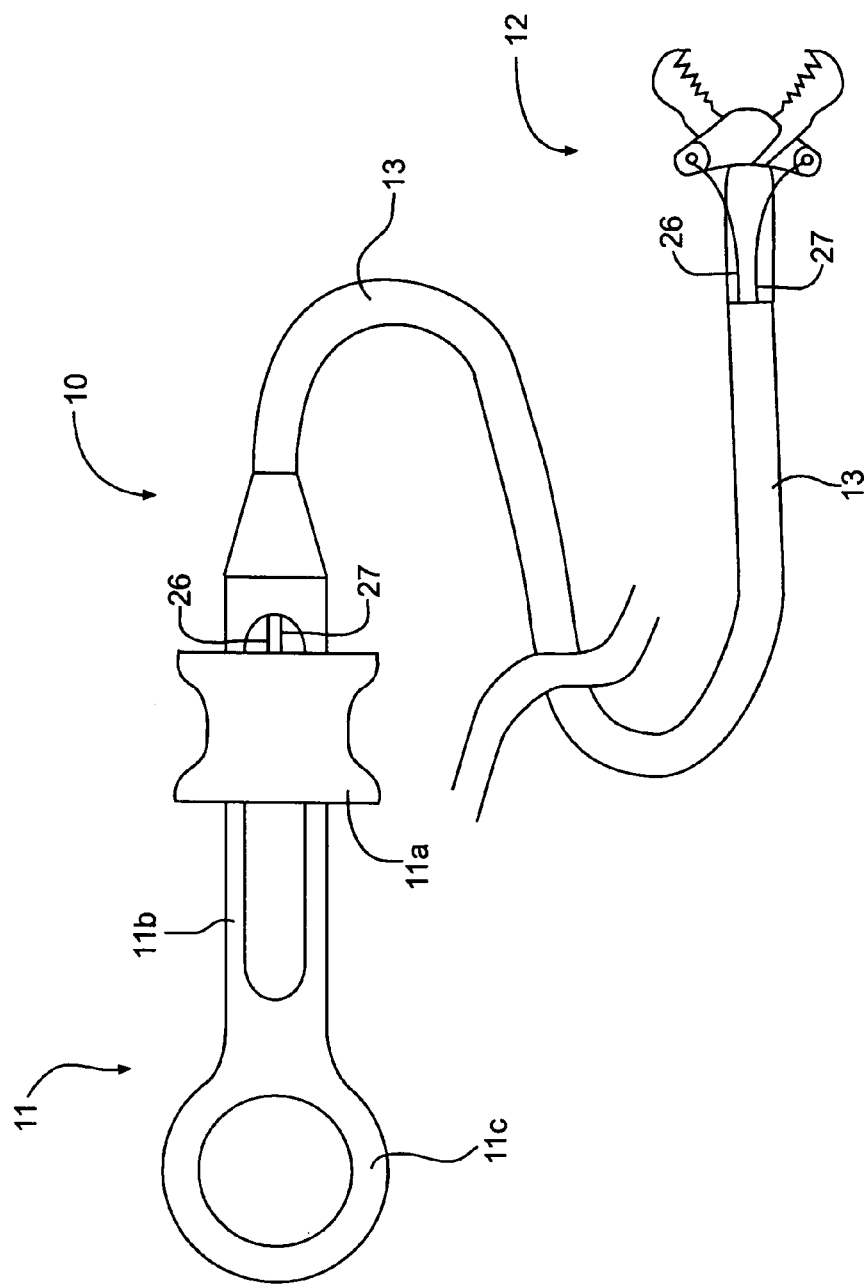
FIG. 1 is a schematic view of a medical instrument according to an embodiment of the present invention.

An exemplary embodiment of an endoscopic instrument 10 is depicted in FIG. 1. The endoscopic instrument 10 includes a handle portion 11 and an end effector assembly 12 connected to each other by a flexible elongate member 13. Control wires 26, 27 extend between the handle portion 11 and the end effector assembly 12 through the flexible elongate member 13.

The handle portion 11 includes a ring portion 11c disposed at the proximal end of an elongate portion 11b. A spool portion 11a is disposed around the elongate portion 11b and is configured to move longitudinally relative to the elongate portion 11b. The spool portion 11a is connected to the control wires 26, 27. The elongate member 13 may include an inner coiled portion 13b (see FIG. 2) surrounded by an outer covering or jacket portion 13a. The inner coiled portion 13b is hollow, and configured to accommodate control wires 26, 27 and allow the longitudinal movement of the control wires 26, 27 therethrough. The handle portion 11 and elongate member 13 described are exemplary only and may have other suitable configurations.

Figure 2:
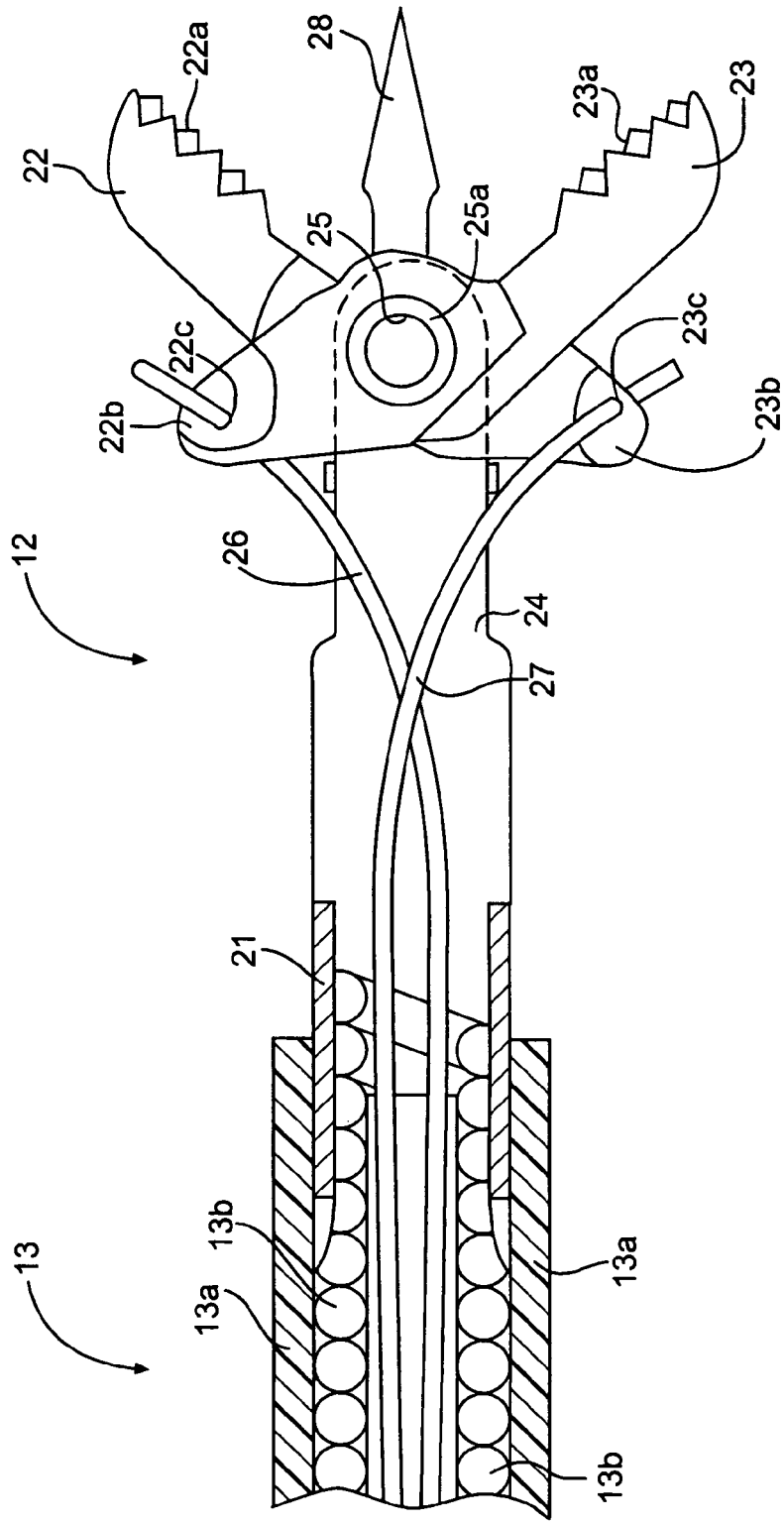
FIG. 2 is a partial cross-sectional view of an end effector assembly of the medical instrument of FIG. 1.

An exemplary embodiment of an end effector assembly 12 is depicted in FIG. 2. The end effector assembly 12 has a clevis 21 which is coupled, on its proximal end to the elongate member 13. The end effector assembly 12 also has a pair of forceps jaws 22, 23 that may be substantially similar in shape and appearance.

The clevis 21 has a pair of clevis arms 24 which accommodate an axle 25 therethrough. Jaws 22, 23 are rotatably mounted on the portion of the axle 25 between the clevis arms 24. Each jaw 22, 23 has a distal cutting edge 22a, 23a, a proximal tang 22b, 23b, and a mounting hole 22c, 23c on the proximal tang 22b, 23b. The proximal tangs 22b, 23b are each coupled to the distal end of a respective control wire 26, 27 which run through the hollow center of the elongate member 13. Manipulation of the handle portion 11, for example the movement of the spool portion 11a relative to the elongate portion 11b, results in the longitudinal movement of the control wires 26, 27 relative to the elongate member 13. The movement of the control wires 26, 27 acts on the proximal tangs 22b, 23b of the jaws 22, 23, resulting in the opening and closing of the jaws 22, 23 relative to each other. The end effector assembly 12 may also include a flat knife or spike 28 which is mounted on the distal end of the clevis 21 and disposed between the jaws 22, 23.

Figure 3A:
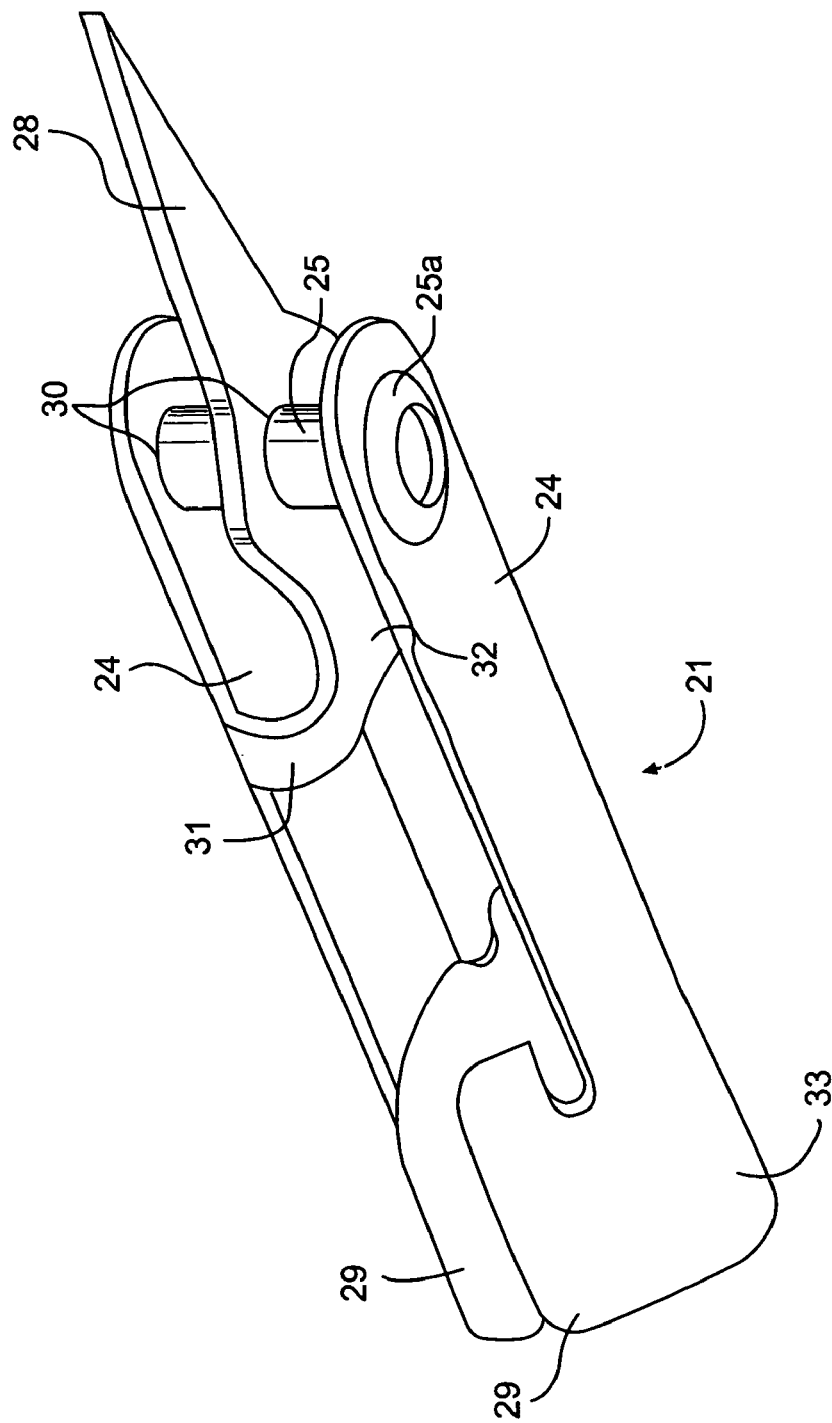
FIG. 3A is a perspective view of a clevis of the end effector assembly of FIG. 2.
Figure 3B:
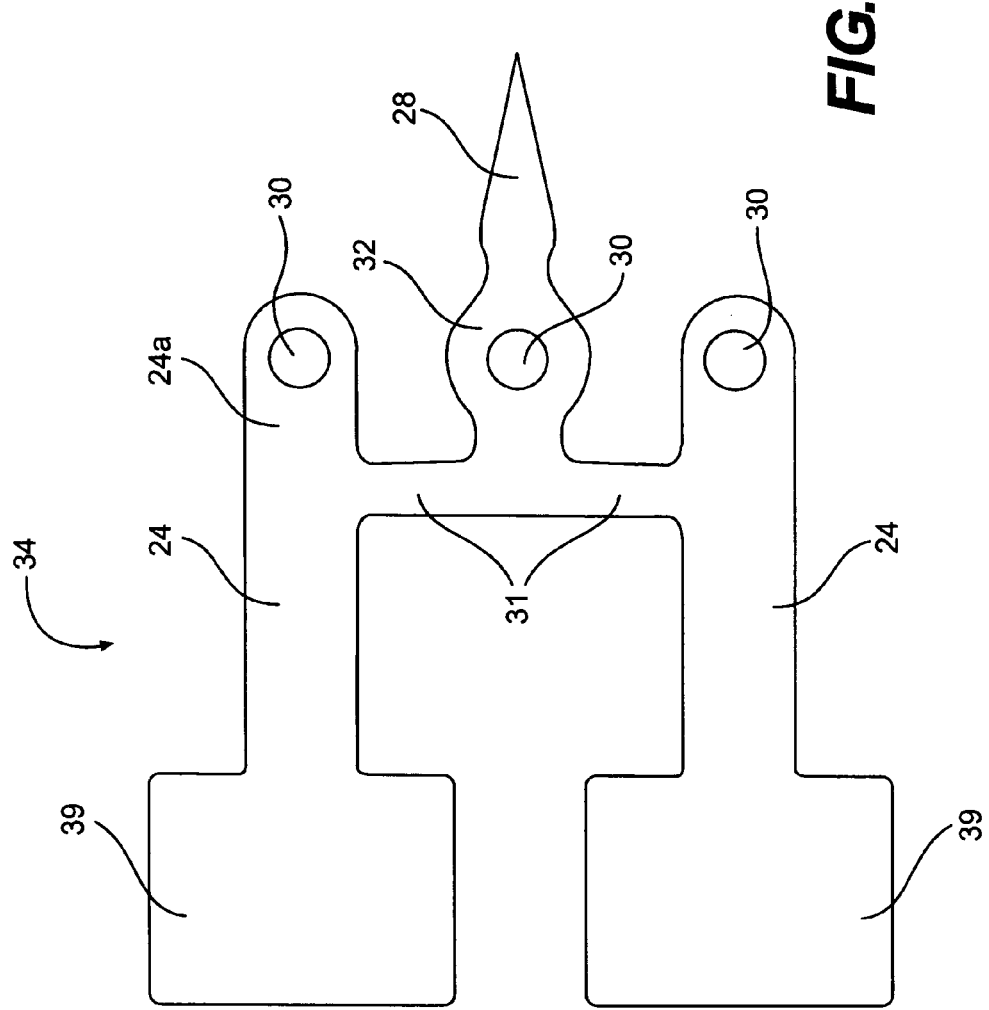
FIG. 3B is a schematic view of a production layout of the clevis of FIG. 3A.
Figure 3C:
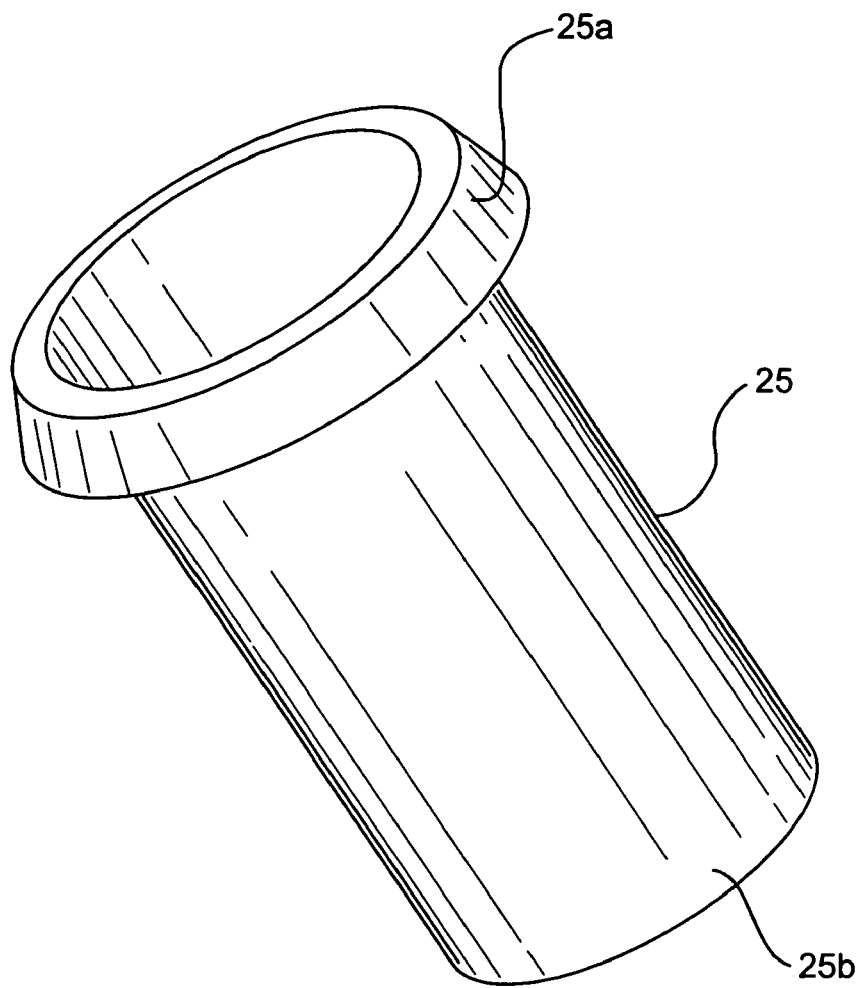
FIG. 3C is a perspective view of an axle for use with the clevis of FIG. 3A.

An exemplary embodiment of a clevis is shown in FIGS. 3A-3C. The clevis 21 may be formed as a unitary molded or cast member. The clevis 21 has a proximal end 29 from which the clevis arms 24 extend, and the proximal end 29 may be configured so that is can be crimped or welded to the distal end of the elongate member 13. For example, the proximal end 29 can be wrapped to form a cylinder or a broken cylinder 33 configured to centrally receive, or be received by, the elongate member 13. Each of the clevis arms 24 have a mounting hole 30 for receiving an axle 25. The clevis arms 24 are joined by a substantially orthogonal cross member 31 disposed distal to the proximal end and proximal to the mounting holes 30. A central tab 32 may extend distally from the cross member 31 to spike 28 and be provided with a third mounting hole 30 that is located at a substantially similar position to the other mounting holes 30 on the clevis arms 24. This third mounting hole 30 may improve stability of the axle 25. The jaws 22, 23 may be mounted on both sides or either side of the central tab 32 with the spike 28 extending between the jaws 22, 23. As will be described in connection with the embodiment of FIGS. 4A-4B, clevis 21 may include stiffening ribs along the arms 24 to provide additional strength and make the arms 24 less flexible in certain directions.

As shown in FIG. 3B, the clevis 21 may be stamped from a stainless steel sheet 34 which is cut (stamped) to form at least two relatively broad proximal bases 39 and at least two relatively narrow substantially parallel clevis arms 24, one arm 24 extending from each base 39. The cut sheet is formed by bending the cross member 31 on either side of the central tab in an "S" configuration so that the mounting holes 30 of each clevis arm 24 and the central tab 32 are aligned substantially coaxially with each other. The steel sheet 34 may also be cut so that a distal spike 28 may extend from the central tab 32. The arms 24 may be bent inward at an angle, for example, of approximately 15 degrees along a portion 24a just proximal of the mounting holes 30. The at least two proximal bases 39 are bent towards each other to form a bifurcated cylinder 33. The bifurcated cylinder 33 can be crimped, welded, or otherwise affixed to the distal end of the elongate member 13.

An axle 25 with one flared end or flange 25a as shown in FIG. 3C is then provided. The axle 25 may have a substantially circular cross-section with a substantially constant inner circumference (e.g., inner diameter) for the entire length of the axle 25. The flared end or flange 25a may also have a substantially circular cross section that tapers from a maximum outer circumference (e.g., outer diameter) at the portion configured to contact an outer surface of the arms 24, to a minimum circumference (e.g., inner diameter) substantially similar to the either the outer circumference of the non-flared portion of the axle 25 or the inner circumference of the axle 25. The end effector assembly 12, for example jaws, may be placed on the axle 25 via the end 25b opposite the flared end or flange 25a. The end effector assembly 12 may be placed on the axle 25 after placing end 25b of the axle 25 through the first mounting hole 30, and then the end 25b may be placed through the other mounting hole 30. In embodiments wherein there is a third arm 24 between the outer arms 24, end 25b may first be placed through one mounting hole 30, a portion of the end effector assembly 12, for example a jaw, may be placed on the axle 25. The end 25b may then be placed through the mounting hole on the central arm 24, the other portion of the end effector assembly 12 may then be placed on the axle 25, and then the end 25b may be placed through the remaining mounting hole 30. At this time, the flared end or flange 25a may contact the outer surface of an arm 24, while the outer surface of the rest of the axle 25 may contact the inner surfaces of the mounting holes 30 and rotate within the mounting holes 30. The other end 25b of the axle 25 is then flared out, or otherwise configured, to lodge the axle 25 in the arms 24 of the clevis 21, making the axle 25 and the end effector assembly 12 relatively difficult to dislodge from the mounting holes 30, for example, during the actuation of the end effector assembly 12. In such a state, portions of the end 25b are in contact with the outer surface of an arm 24 and flared out portions of the end 25b may also be disposed within the adjacent mounting hole 30 (i.e., the circumference of the end 25b in the mounting hole 30 may increase and form a press-fit with the mounting hole 30 due to the flaring out of the rest of the end 25b).

In various embodiments, the inner portion of the axle 25 may be hollow or solid, and may have any desired cross-sectional shape, and may even have a cross-sectional shape that varies along its length. The outer surface of the axle 25 may not be smooth. That surface may have grooves or other features, for example, to assist in the alignment of portions of the end effector assembly 12 on the axle 25. That surface may also have a roughened surface at certain portions to interact with portions of the clevis 21 defining holes 30 and thereby limit its rotational motion relative to those arms. The flared end or flange 25a may not be disposed around the entire circumference of an end of the axle 25, but may instead be a tab or a plurality of tabs disposed around the end of the axle 25 that function substantially similarly to the flange 25a. In addition to being flared out, the other end 25b of the axle 25 may be threaded so that a nut may be screwed on, may be configured to be riveted, or may be configured to accept an adhesive.

The design of the axle 25 and its use during the forming of clevis 21 may improve manufacturability of the end effector assembly 12 by utilizing the placement of the axle 25 in the mounting holes 30 as an alignment aid, if necessary, for the clevis 21 and the jaws 22, 23. Furthermore, by flaring out each end 25a, 25b of the axle 25, the axle 25, and anything mounted to the axle 25, for example, the jaws 22, 23, may be prevented from axially shifting in the mounting holes 30. However, in some cases, it may be desirable to flare out the ends 25a, 25b of the axle 25 in a manner so as to allow axial shifting of the axle 25 and/or the jaws 22, 23 in the mounting holes 30.

The design of the axle 25 with a flared end 25a may improve the manufacturability of the axle 25 by utilizing the central orifice of the axle 25 as an alignment in the production of the axle 25. For example, manufacturability may be improved because the design of the axle 25 may ensure riveting accuracy axially. With this design of the axle 25 with an orifice, rework or replacement of the axle 25 is possible during manufacturing, possibly avoiding disposal of the entire axle or device.

Figure 4A:
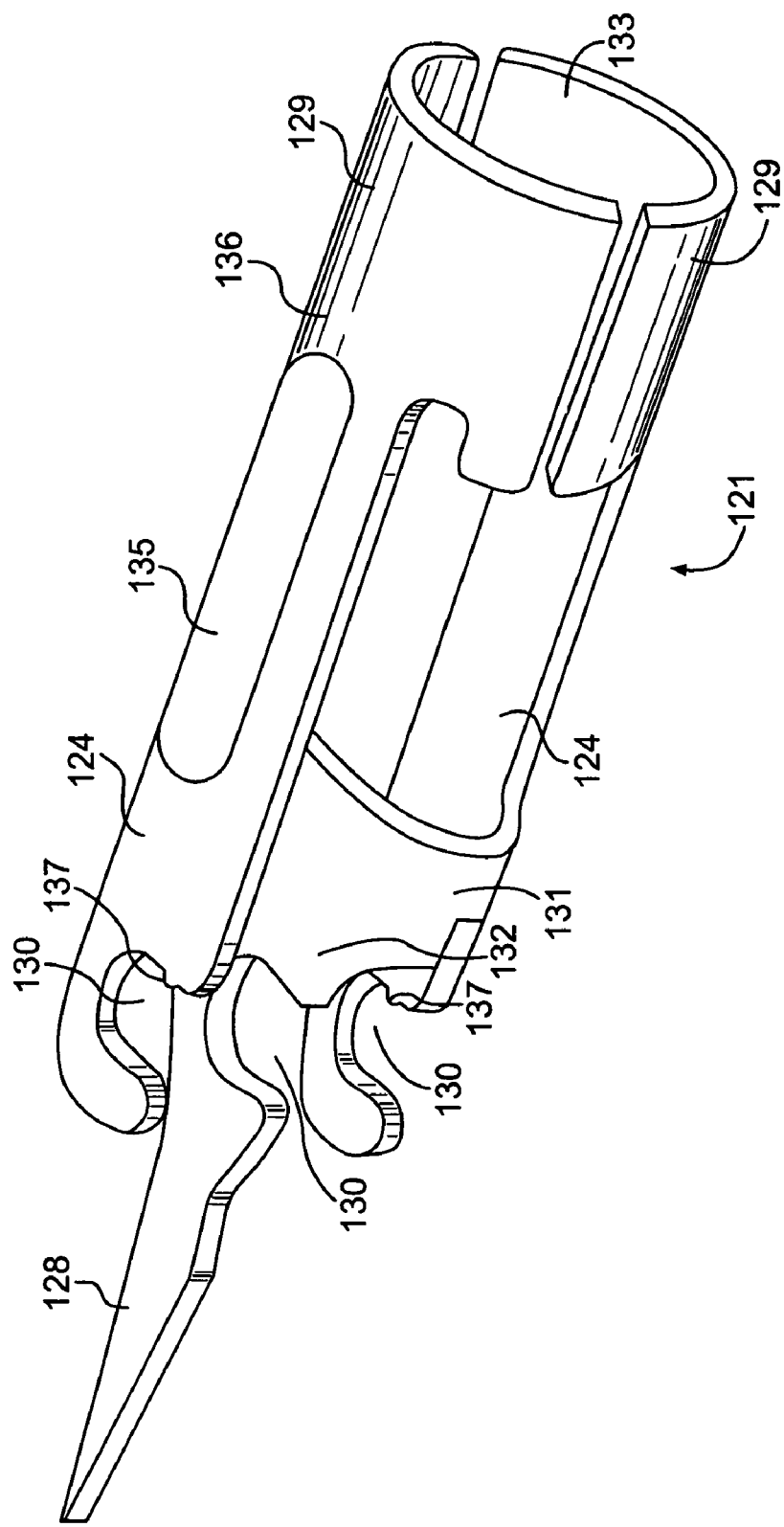
FIG. 4A is a perspective view of a clevis of an end effector assembly for us in a medical instrument, according to another embodiment of the present invention.
Figure 4B:
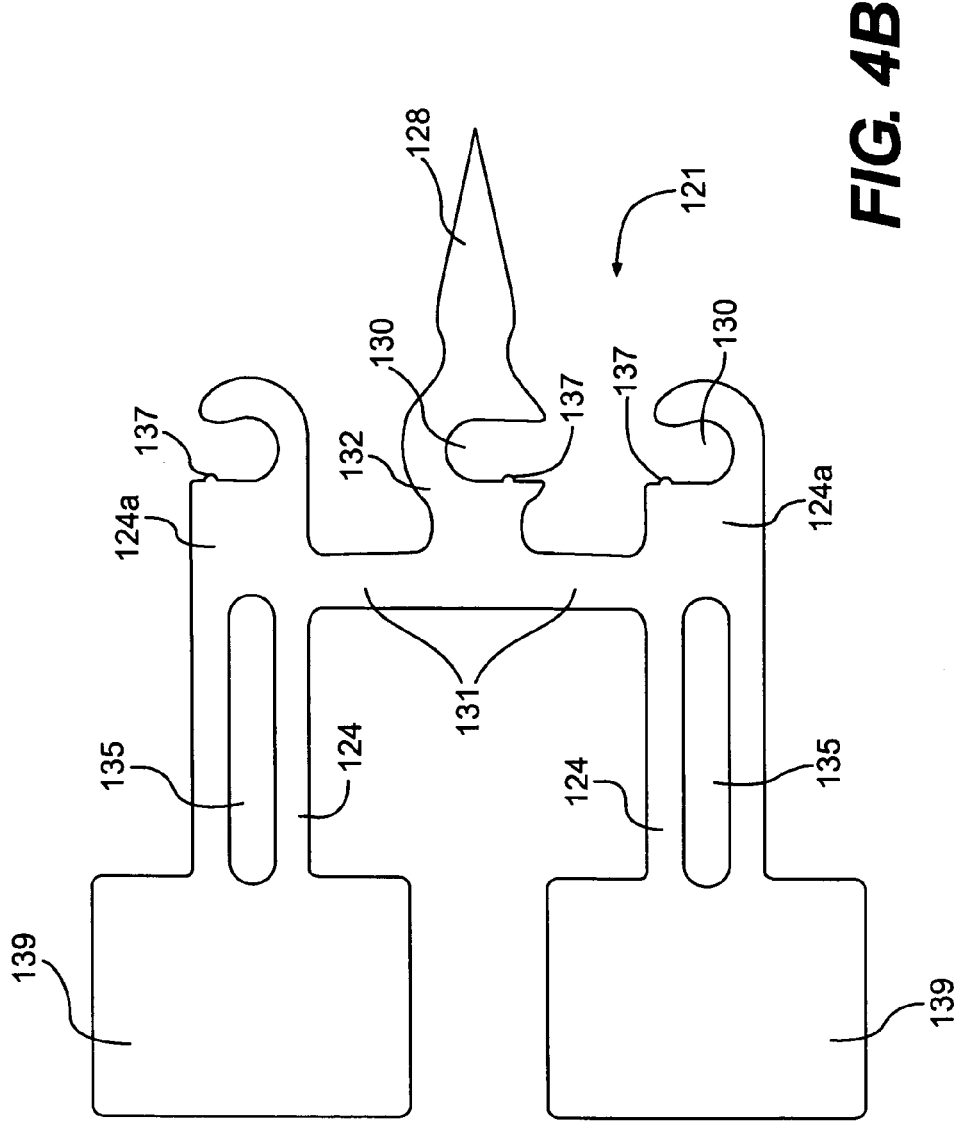
FIG. 4B is a schematic view of a production layout of the clevis of FIG. 4A.

Another exemplary embodiment of a clevis is shown in FIGS. 4A-4B. The clevis 121 is formed as a unitary molded or cast member and has a substantially cylindrical proximal end 129 from which the clevis arms 124 extend. The proximal end 129 of the clevis 121 is wrapped to form a cylinder or a broken cylinder 133, and may be crimped, welded, or otherwise affixed to the distal end of the elongate member 13. The clevis arms 124 each define at least one U-shaped groove 130 for receiving an axle pin 125 shown in FIG. 4C. The clevis arms 124 are joined by a substantially orthogonal cross member 131 disposed proximal to the U-shaped grooves 130. A central tab 132 may extend distally from the cross member 131 and be provided with a third U-shaped groove 130. The jaws 22, 23 may be mounted on both sides or either side of the central tab 132 with a spike 128 extending between the jaws 22, 23. The clevis arms 121 may also include stiffening ribs 135 on the outside surfaces 136 of each of the clevis arms 121 so as to provide additional strength, and make the arms 121 less flexible in certain directions.

As shown in FIG. 4B, the clevis 121 may be stamped from a stainless steel sheet 134 which is cut (stamped) to form at least two relatively broad proximal bases 139 and at least two relatively narrow substantially parallel clevis arms 124, one arm 124 extending from each base 139. The cut sheet is formed by bending the cross member 131 on either side of the central tab in an "S" configuration so that the U-shaped grooves 130 of each clevis arm 124 and the central tab 132 are aligned substantially coaxially with each other. The steel sheet 134 may also be cut so that a distal spike 128 may extend from the central tab 132. The arms 124 may be bent inward at an angle, for example, of approximately 15 degrees along a portion 124a just proximal of the U-shaped grooves 130. The at least two proximal bases 139 are bent towards each other to form a bifurcated cylinder 133. The bifurcated cylinder 133 can be crimped, welded, or otherwise affixed to the distal end of the elongate member 13.

Figure 4C:
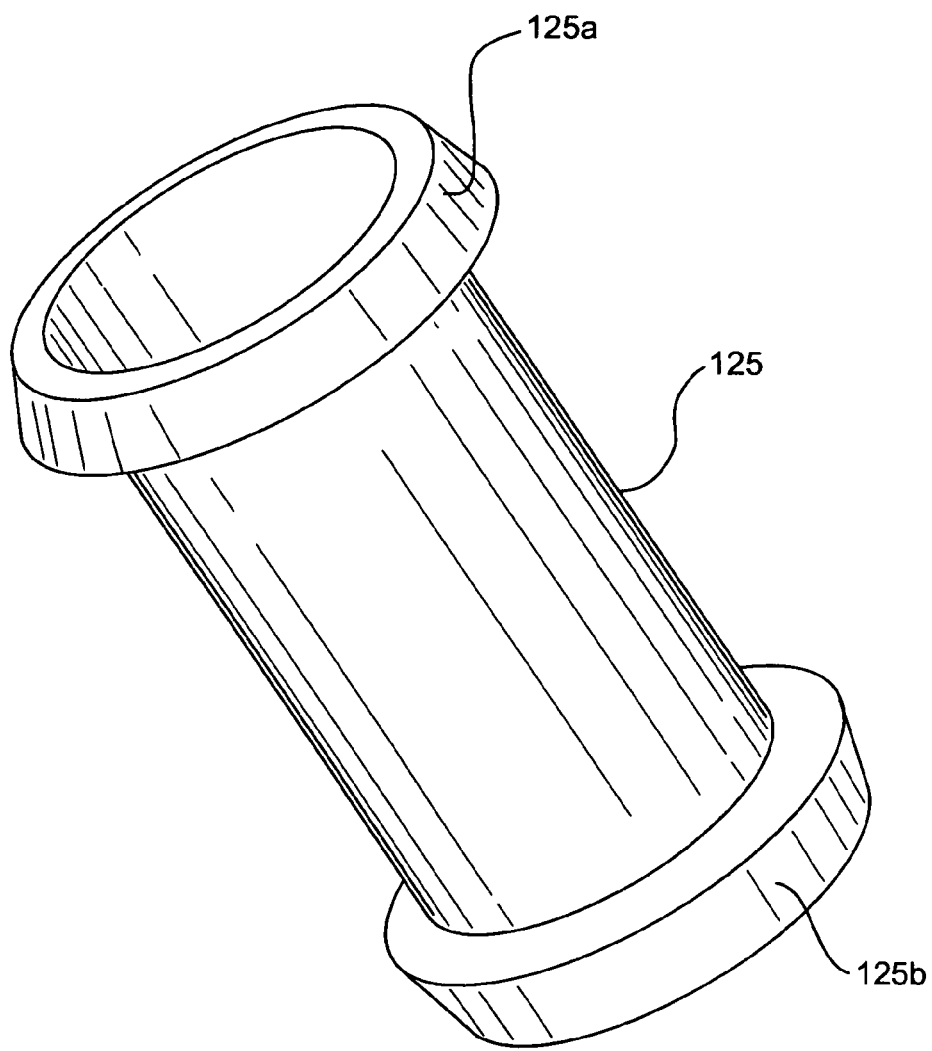
FIG. 4C is a perspective view of an axle for use with the clevis of FIG. 4B.

The U-shaped grooves 130 are configured to receive and retain an axle pin 125, for example, as depicted in FIG. 4C, configured to accommodate the jaws 22, 23. The axle pin 125 may be snapped or otherwise affixed into place in the U-shaped grooves 130. For example, the U-shaped grooves 130 may have protrusions or bumps 137 (shown in FIG. 4B) on the inside portions of their ends configured to retain the axle pin 125. Bumps 137 would overlie pin 125 once pin 125 is in place within grooves 130. Alternatively or additionally, pin 125 may be bonded within grooves 130 with a suitable biocompatible adhesive. Other contemplated methods of retaining the axle pin include spot welding, seam welding, brazing, resistance welding of contact areas, and any other method known in the art.

The jaws 22, 23 may be placed on the axle pin 125, and then the axle pin 125 may be placed in the U-shaped grooves 130, simplifying the process of both installing the jaws 22, 23 and aligning axle pin 125 in the U-shaped grooves 130. As in the embodiment of FIGS. 3A-3C, this configuration is also tolerant of slight axial misalignments of the U-shaped grooves 130 during the bending of the sheet 134.

The stiffening ribs 135 may be stamped on the sheet 134, and displace some of the material on the inside surface 138 of the sheet to the outside surface 136. This configuration imparts greater stability on the arms 124, and makes it more resistant to bending or torqueing either due to outside forces, or due to the actuation of the end effector assembly 112.

The pin 125 may have a substantially circular cross-section with a substantially constant inner circumference (e.g., inner diameter) for the entire length of the pin 125. The flared ends or flanges 125a, 125b may also have a substantially circular cross section that tapers from a maximum outer circumference (e.g., outer diameter) at the portion configured to contact an outer surface of the arms 24, to a minimum circumference (e.g., inner diameter) substantially similar to either the outer circumference of the non-flared portion of the pin 125 of the inner circumference of the pin 125. The end effector assembly 12, for example jaws, may be placed on the pin 125, and then the pin 125 may be inserted into the grooves 130. At this time, the flared ends or flanges 125a, 125b may contact the outer surface of an arm 24, while the outer surface of the rest of the pin 125 may contact the inner surfaces of the grooves 130 and rotate within the grooves 130. In such a state, the pin 125 and the end effector assembly 12 may be relatively difficult to dislodge from the grooves 30, for example, during the actuation of the end effector assembly 12. Portions of the pin 125 may also be in contact with bumps or protrusions 137 which may assist in retaining the pin 125 in the grooves 130.

In various embodiments, the inner portion of the pin 125 may be hollow or solid, and may have any desired cross-sectional shape, and may even have a cross-sectional shape that varies along its length. The outer surface of the pin 125 may not be smooth. That surface may have grooves or other features, for example, to assist in the alignment of portions of the end effector assembly 12 on the pin 125. That surface may also have a roughened surface at certain portions to interact with portions of the clevis 121 defining U-shaped grooves 130 and thereby limit its rotational motion relative to those arms 124. The flared ends or flanges 125a, 125b may not be disposed around the entire circumference of an end of the pin 125, but may instead be a tab or a plurality of tabs disposed around the ends of the pin 125 that function substantially similarly to the flange 25a in FIG. 3C. Furthermore, instead of being flared out, either end 125a, 125b of the pin 125 may be threaded so that a nut may be screwed on, may be configured to be riveted, or may be configured to accept an adhesive.

There have been described and illustrated herein several embodiments of a clevis for an endoscopic instrument and methods of making the same. While particular embodiments of the invention have been described, it is not intended that the invention be limited thereto, as it is intended that the invention be as broad in scope as the art will allow and that the specification be read likewise.

Thus, while particular materials have been disclosed, it will be appreciated that other materials could be utilized. For example, the disclosed clevises may be formed of any suitable biocompatible material including various metals and non-metals. In addition, while cylindrical portions have been shown as incomplete or broken cylinders, it will be recognized that welding, soldering, brazing, or other operations may be used to complete the cylindrical portions if desired. For example, the clevis and end effector may not only be stamped out of steel, but may also be cast, molded, or machined out of bronze, plastics, metals, ceramics, or other suitable materials known in the art. Additionally, the jaws may be substantially similar in shape to each other, however, they may also be different in configuration from each other.

In a further example, while the clevis is shown with respect to use in a biopsy forceps instrument, the clevis could be used with any of a variety of end effectors as part of any endoscopic or non-endoscopic medical device, including, for example, clamp, scissors, dissectors, graspers, etc. In various embodiments, the invention is not limited to use in endoscopic procedures or medical instruments, but may also be used in any other medical procedure (e.g., gastrointestinal, urological, gynecological, cardiological, etc.) or non-medical procedure, or in medical or non-medical instruments.

Moreover, while particular configurations have been disclosed in reference to the mounting holes and the spike, other configurations could be used as well. In yet another example, any of the features disclosed in the specification may be rearranged to be on any other portion disclosed in the specification. For example, a clevis may have arms where at least one of the arms has a mounting hole, while at least one other arm has a U-shaped grooves. It will therefore be appreciated by those skilled in the art that yet other modifications could be made to the provided invention without deviating from its spirit and scope as so claimed.

Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A clevis assembly for a medical instrument comprising:
a clevis having a base and a plurality of arms extending from the base; and
an axle to extend between the plurality of arms,
wherein each of the plurality of arms is configured to accommodate a portion of the axle,
wherein an end of the axle includes a flared portion to engage a first outer surface of one of the plurality of arms,
wherein the axle has a deformed portion at an end of the axle opposite the flared portion,
wherein the deformed portion lies on a second outer surface of another of the plurality of arms, and
wherein the second outer surface is not a surface facing a hole or a U-shaped groove to receive the axle, the hole or U-shaped groove being defined by the another of the plurality of arms.

2. The assembly of claim 1, wherein the axle is configured to accommodate at least a portion of an end effector assembly.

3. The assembly of claim 1, wherein the flared portion engages the first outer surface of one of the plurality of arms so as to prevent the axle from moving longitudinally relative to the plurality of arms.

4. The assembly of claim 1, wherein each of the plurality of arms defines a hole to receive the axle.

5. The assembly of claim 1, wherein the flared portion is a flange.

6. The assembly of claim 1, wherein each of the plurality of arms defines a U-shaped groove to receive the axle.

7. The assembly of claim 1, wherein the one of the plurality of arms defines a hole and another of the plurality of arms defines a U-shaped groove, the hole and groove for receiving the axle.

8. The assembly of claim 1, further comprising a reinforcing portion on at least one of the plurality of arms.

9. The assembly of claim 8, wherein the reinforcing portion includes a portion of the arm displaced outwardly.

10. The assembly of claim 1, wherein the deformed portion is formed after the axle has been placed through the plurality of arms.

11. The assembly of claim 1, wherein the first outer surface is directing away from the one of the plurality of arms.

12. The assembly of claim 1, wherein the first and second outer surfaces are substantially flat.

13. The assembly of claim 1, wherein the first and second outer surfaces are orthogonal to an axis of the axle.

14. A medical instrument comprising:
a handle portion;
an end effector assembly; and
an elongate member connecting the handle portion to the end effector assembly,
wherein the end effector assembly comprises:
a clevis having a base and a plurality of arms extending from the base; and
an axle to extend between the plurality of arms;
wherein each of the plurality of arms is configured to accommodate a portion of the axle,
wherein an end of the axle includes a flared portion to engage a first outer surface of one of the plurality of arms,
wherein the axle has a deformed portion at an end of the axle opposite the flared portion,
wherein the deformed portion lies on a second outer surface of another of the plurality of arms, and
wherein the second outer surface is not a surface facing a hole or a U-shaped groove to receive the axle, the hole or U-shaped groove being defined by the another of the plurality of arms.

15. The medical instrument of claim 14, wherein the axle is configured to accommodate at least a portion of the end effector assembly.

16. The medical instrument of claim 14, wherein the flared portion engages the first outer surface of one of the plurality of arms so as to prevent the axle from moving longitudinally relative to the plurality of arms.

17. The medical instrument of claim 14, wherein each of the plurality of arms defines a hole to receive the axle.

18. The medical instrument of claim 14, wherein the flared portion is a flange.

19. The medical instrument of claim 14, wherein each of the plurality of arms defines a U-shaped groove to receive the axle.

20. The medical instrument of claim 14, wherein the one of the plurality of arms defines a hole and another of the plurality of arms defines a U-shaped groove, the hole and groove for receiving the axle.

21. The medical instrument of claim 14, further comprising a reinforcing portion on at least one of the plurality of arms.

22. The medical instrument of claim 21, wherein the reinforcing portion includes a portion of the arm displaced outwardly.

23. The medical instrument of claim 14, wherein the end effector assembly further comprises a pair of jaws.

24. The medical instrument of claim 14, wherein the handle portion includes an elongate portion and a spool portion slidably disposed around the elongate portion.

25. The medical instrument of claim 14, wherein the elongate member includes a jacket covering a hollow coiled portion.

26. The medical instrument of claim 14, wherein the deformed portion is formed after the axle has been placed through the plurality of arms.

27. The medical instrument of claim 14, wherein the first outer surface is directing away from the one of the plurality of arms.

28. The medical instrument of claim 14, wherein the first and second outer surfaces are substantially flat.

29. The medical instrument of claim 14, wherein the first and second outer surfaces are orthogonal to an axis of the axle.

* * * * *

UNITED STATES PATENT AND TRADEMARK OFFICE
CERTIFICATE OF CORRECTION

| | | |
|---|---|---|
| PATENT NO. | : 7,534,253 B2 | Page 1 of 1 |
| APPLICATION NO. | : 10/731153 | |
| DATED | : May 19, 2009 | |
| INVENTOR(S) | : Endara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1011 days.

Signed and Sealed this

Twenty-eighth Day of September, 2010

David J. Kappos
*Director of the United States Patent and Trademark Office*